(12) United States Patent
Ge et al.

(10) Patent No.: US 10,458,918 B2
(45) Date of Patent: Oct. 29, 2019

(54) SUBSTANCE DETECTION DEVICE

(71) Applicant: Hewlett-Packard Development Company, L.P., Houston, TX (US)

(72) Inventors: Ning Ge, Palo Alto, CA (US); Steven Barcelo, Palo Alto, CA (US); Charles M Santori, Palo Alto, CA (US); Helen A Holder, Palo Alto, CA (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 0 days.

(21) Appl. No.: 15/764,324

(22) PCT Filed: Nov. 13, 2015

(86) PCT No.: PCT/US2015/060686
§ 371 (c)(1),
(2) Date: Mar. 29, 2018

(87) PCT Pub. No.: WO2017/082930
PCT Pub. Date: May 18, 2017

(65) Prior Publication Data
US 2018/0284027 A1    Oct. 4, 2018

(51) Int. Cl.
*G01N 21/03*    (2006.01)
*G01N 21/65*    (2006.01)

(52) U.S. Cl.
CPC ........... *G01N 21/658* (2013.01); *G01N 21/03* (2013.01)

(58) Field of Classification Search
CPC ............... G01N 21/658; G01N 21/648; G01N 2021/6482; G01N 2021/651; G01N 2035/00425; G01N 2035/1034; G01N 2035/1048; G01N 21/03; G01N 21/645; G01N 27/622; G01N 35/1004; G01N 35/1009; G01N 15/0272; G01N 15/06; G01N 1/28; G01N 2015/0065; G01N 2021/0364; G01N 21/0303; G01N 21/11; G01N 21/65; G01N 2201/0638; G01N 27/624; G01J 3/44; G02B 3/02

See application file for complete search history.

(56) References Cited

U.S. PATENT DOCUMENTS 7,391,511 B1    6/2008 Bratkovski et al.
7,651,863 B2    1/2010 Hulteen et al.
(Continued)

FOREIGN PATENT DOCUMENTS

WO    WO-2010073260 A1    7/2010
WO    WO-2013-048446 A1    4/2013
WO    WO-2014-142912 A1    9/2014

OTHER PUBLICATIONS

Baca, A.J. et al.; Mosaic-like Silver Nanobowl Plasmonic Crystals as Highly Active Surface-enhanced Raman Scattering Substrates; Jul. 27, 2015; http://pubs.acs.org/doi/abs/10.1021/acs.jpcc.5b03824?journalCode=jpccck.

*Primary Examiner* — Michael P Stafira
(74) *Attorney, Agent, or Firm* — Dierker & Kavanaugh PC

(57) ABSTRACT

In an example implementation, a substance detection device includes a substrate having nanoimprinted chamber walls and nanostructures. The chamber walls define a chamber and the nanostructures are positioned within the chamber to react to a substance introduced into the chamber. A two-dimensional (2D) orifice plate is affixed to the chamber walls and forms a top side of the chamber.

15 Claims, 4 Drawing Sheets

(56) References Cited

U.S. PATENT DOCUMENTS

| | | | |
|---|---|---|---|
| 7,929,133 B2 | 4/2011 | Wang et al. | |
| 2005/0258359 A1* | 11/2005 | Guevremont | H01J 49/0018 |
| | | | 250/288 |
| 2010/0159616 A1 | 6/2010 | Park et al. | |
| 2011/0267609 A1 | 11/2011 | Wu et al. | |
| 2012/0300203 A1 | 11/2012 | Tyagi et al. | |
| 2014/0218727 A1 | 8/2014 | Li et al. | |
| 2015/0204792 A1 | 7/2015 | Shibayama et al. | |
| 2016/0003732 A1* | 1/2016 | Li | G01N 21/648 |
| | | | 356/301 |
| 2016/0025635 A1* | 1/2016 | Li | G01N 21/658 |
| | | | 422/82.01 |

* cited by examiner

SUBSTANCE DETECTION DEVICE

BACKGROUND

Surface Enhanced Raman Spectroscopy (SERS) may be used in various industries to detect the presence of an analyte. For example, SERS may be used in the security industry to detect and/or scan for explosives (e.g., detecting and/or scanning baggage at airports for explosives and/or other hazardous materials). Alternatively, SERS may be used in the food industry to detect toxins or contaminants in water and/or milk.

BRIEF DESCRIPTION OF THE DRAWINGS

Examples will now be described with reference to the accompanying drawings, in which.

Throughout the drawings, identical reference numbers designate similar, but not necessarily identical, elements.

DETAILED DESCRIPTION

Figure 1:
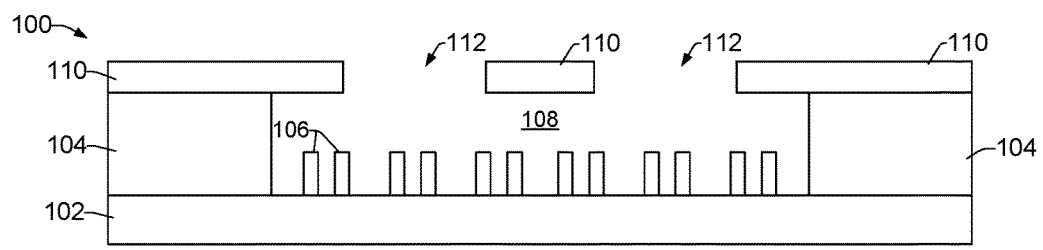
FIG. 1 shows an example of a substance detection device.

The integration of SERS technology into microfluidic devices such as lab-on-a-chip (LOC) devices has applicability across a range of industries, including various life science and other industries for purposes such as biomedical diagnostics, drug development, DNA replication, and so on. Such testing devices can include substrates with nanostructures to facilitate the measurement of liquid samples, for example, to identify various substances. Protecting the substrate and nanostructures within such a test device from premature exposure to the environment and/or a substance (e.g., an analyte) that the substrate is intended to detect, can involve attaching the substrate to a housing such as a three-dimensional (3D) metal orifice plate. The 3D orifice plate/housing can define a chamber having chamber walls and a chamber top that surround and protect a portion of the substrate and nanostructures. During testing, a sample can be introduced into the chamber through an opening in the 3D orifice plate, exposing the substrate and nanostructures to a substance of interest within the sample.

In some applications, producing SERS testing devices using a roll-to-roll production method with a flexible substrate can be cost-effective. However, while a 3D orifice plate can protect the substrates and nanostructures of such testing devices, a roll-to-roll production of the flexible substrate with the 3D orifice plate can be challenging. During roll-to-roll production, the rigid shape of a 3D metal orifice plate can reduce the degree to which a firm attachment can be made between the orifice plate and the flexible substrate. Stress at the bonding points where the chamber walls of the rigid 3D orifice plate meet the flexible substrate can be weakened during roll-to-roll production.

Accordingly, examples of a substance detection device and methods of making/fabricating a substance detection device are described herein. In various examples, a nanoimprint process includes the use of a patterned mold or "imprint stamp" to imprint both the nanostructures and the walls of a chamber onto a flexible substrate of a device. The smaller nanostructures are positioned within the chamber defined by the larger chamber walls, and a rigid, two-dimensional (2D) orifice plate is applied to the tops of the chamber walls to cover the chamber. A removable barrier such as a tape sealing is applied to the 2D orifice plate to close openings in the plate and protect the substrate and nanostructures within the chamber. The rigid, 2D orifice plate and the flexible substrate with nanoimprinted chamber walls form a partly rigid and partly flexible device that provides for effective, low cost, roll-to-roll production. Furthermore, the rigid, 2D orifice plate helps prevent damage from removal of the barrier (e.g., removal of the tape sealing) and provides accurate distance control for focusing a reading device due to reduced bending or bowing when compared to a device having a totally flexible structure.

In an example implementation, a substance detection device includes a substrate comprising nanoimprinted chamber walls and nanostructures. The nanoimprinted chamber walls define a chamber in which the nanostructures are positioned. The device also includes a two-dimensional (2D) orifice plate affixed to the chamber walls. The 2D orifice plate forms a top side of the chamber. The nanostructures are to react to a substance introduced into the chamber (e.g., through an opening in the 2D orifice plate).

In another example implementation, a method of making a substance detection device includes imprinting chamber walls and nanostructures onto a substrate. The chamber walls define a chamber in which the nanostructures are positioned. The method also includes affixing a two-dimensional (2D) orifice plate to the chamber walls, the orifice plate forming a top to the chamber.

In another example implementation, a partly rigid and partly flexible substance detection device includes a flexible substrate. The flexible substrate has chamber walls and nanostructures that are nanoimprinted onto the substrate. The chamber walls define a chamber in which the nanostructures are positioned. The partly rigid and partly flexible substance detection device also includes a rigid metal two-dimensional (2D) orifice plate bonded to the chamber walls. The rigid metal 2D orifice plate forms a top side of the chamber.

Figure 2:
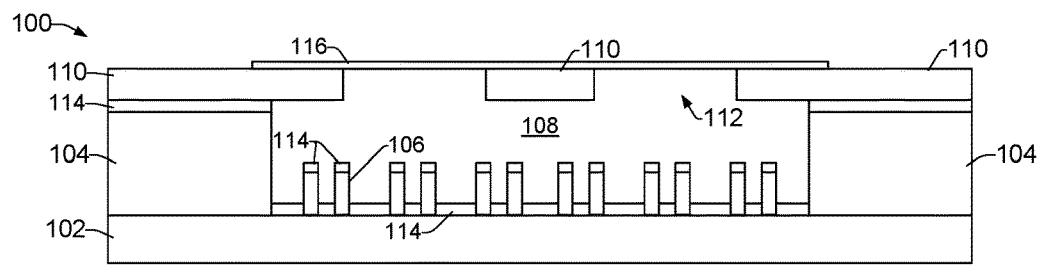
FIG. 2 shows an example of a substance detection device with additional details of components of the device.

FIG. 1 is an illustration of an example substance detection device 100 showing some of the components of the device. FIG. 2 is an illustration of the example substance detection device 100 showing some additional details of components of the device. As shown in FIGS. 1 and 2, an example substance detection device 100 includes a substrate 102 comprising nanoimprinted chamber walls 104 and nanostructures 106. The substrate 102 can be made of any suitable flexible material such as glass, plastic, Polydimethylsiloxane, a transparent material, rubber and/or a membrane, for example. The nanoimprinted chamber walls 104 and nanostructures 106 can be made of an imprintable material such as a polymer imprint resist material. The imprintable material comprises a curable material such as a photo (UV) or thermal curable polymer resist.

The nanoimprinted chamber walls 104 define a chamber 108 in which the nanostructures 106 are positioned. In some examples, the nanostructures 106 may be referred to variously as nano-fingers, nano-pillars, sensing fingers, sensing pillars, and so on. The nanostructures 106 are to react to a substance when exposed to the substance within the chamber 108, for example, when a liquid sample containing the substance is introduced into the chamber 108.

In addition to defining the chamber 108, the chamber walls 104 support a two-dimensional (2D) orifice plate 110 affixed to the top sides of the chamber walls 104. The 2D orifice plate 110 forms a top side of the chamber 108. In some examples, a sample containing a substance of interest can be introduced into the chamber 108 through an opening 112 in the 2D orifice plate 110. The 2D orifice plate 110 comprises a rigid plate that can be made of any suitable material such as metal, nickel, gold and/or platinum, for example. The 2D orifice plate 110 can be formed, for example, in an electroplating process in which a mandrel is immersed in a plating bath that plates a surface of the mandrel with a metal material (e.g., nickel, gold, platinum, etc.) everywhere except where a nonconductive material such as silicon carbide is located. The metal from the plating bath defines patterns, shapes and/or features of the orifice plate 110, such as openings 112. After the mandrel and the orifice plate 110 are removed from the plating bath, the orifice plate 110 can be removed and/or peeled off of the mandrel.

As shown in FIG. 2, an example substance detection device 100 can include a layer of material 114 deposited over the substrate 102. The layer 114 comprises a sensing material layer 114 that can be deposited, for example, by sputtering the sensing material onto the substrate 102 to cover the tops of the nanostructures 106 and chamber walls 104, and the areas in between the nanostructures 106 and chamber walls 104. The sensing material layer 114 can be formed of nanoparticles including gold and/or silver and/or any other element or chemical that may react with, respond to, collect, etc., a substance of interest such as an analyte. Thus, in one aspect, the material layer 114 is deposited onto the nanostructures 106 to facilitate sensing of a substance. In another aspect, the material layer 114 is deposited onto the top sides of the chamber walls 104 to facilitate bonding of the 2D orifice plate 110 to the chamber walls 104.

In addition to a sensing material layer 114, FIG. 2 shows the example substance detection device 100 as including a removable barrier 116 covering at least a portion of the 2D orifice plate 110. The removable barrier 116 comprises a removable seal 116 to enclose the chamber 108 and protect the substrate 102 and nanostructures 106 from premature exposure to the environment and/or a substance of interest. The removable seal 116 comprises a hermetic seal that can be made of, for example, polymer tape, plastic material, transparent material, plastic sheeting, foil material (e.g., aluminum, copper, tin, gold), foil sheeting, a membrane, wax and/or Polydimethylsiloxane, and so on. In some examples the removable seal 116 comprises a transparent seal to enable a reading device to take measurements of the nanostructures 106 and/or nanoparticles in the sensing material layer 114 while the seal 116 is attached to the 2D orifice plate 110.

Figure 3:
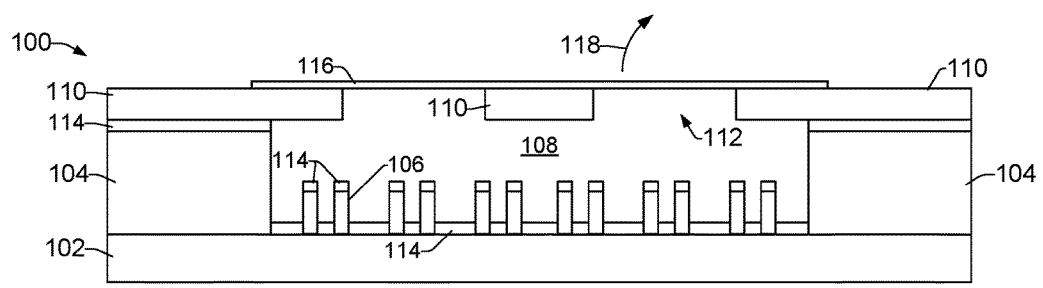
FIG. 3 shows an example of a substance detection device with a removable seal about to be removed.
Figure 4:
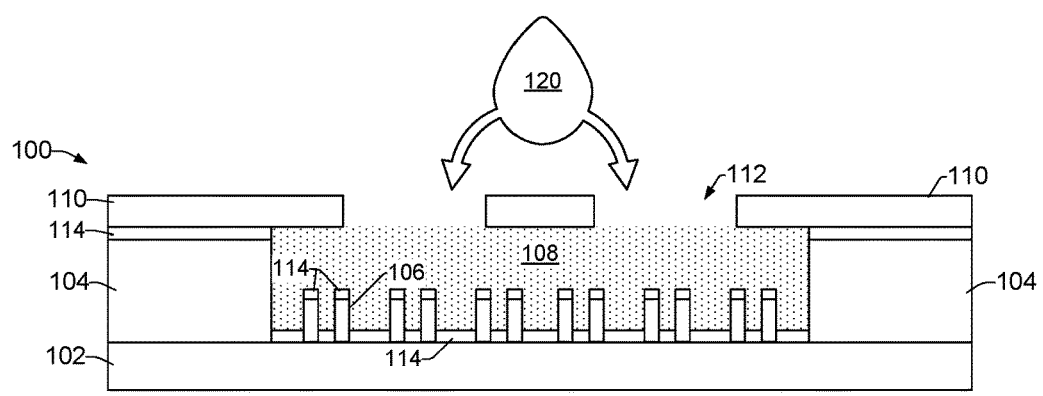
FIG. 4 shows an example of a substance detection device with a seal removed from a two-dimensional orifice plate and a sample to be analyzed added to a chamber.

FIG. 3 shows an example substance detection device 100 with the removable seal 116 about to be removed in a direction generally indicated by arrow 118. As shown in FIG. 4, after the seal 116 is removed from the 2D orifice plate 110 of the substance detection device 100, a sample 120 of liquid solution and/or air or other gas within a test environment (e.g., a room) in which the device 100 is positioned can flow through the openings 112 and into the chamber 108 where it is exposed to the nanostructures 106 and/or nanoparticles in the sensing material layer 114. The sample 120 may or may not include the analyte/substance that the nanostructures 106 and/or nanoparticles of the sensing material layer 114 are intended to detect. In some examples, after the sample 120 is added to the chamber 108, a portion of the sample 120 evaporates leaving particles of a substance of interest on the nanostructures 106 and/or nanoparticles of the sensing material layer 114. In some examples, after the nanostructures 106 and/or nanoparticles in the sensing material layer 114 have been exposed to the sample 120, the chamber 108 can be covered again by the seal 116 and/or another seal to ensure that the nanostructures 106 and/or nanoparticles in the sensing material layer 114 are not contaminated through exposure to a non-testing environment after the test has occurred.

Figure 5:
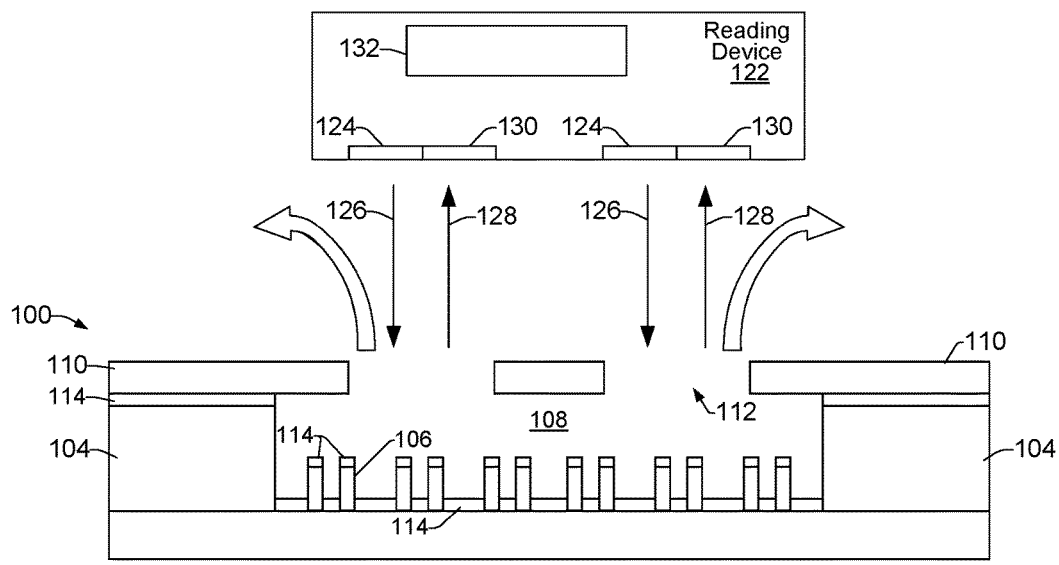
FIG. 5 shows an example of a substance detection device and an example reading device to analyze and detect a substance of interest within a chamber of the device.

FIG. 5 shows an example substance detection device 100 and an example reading device 122 to analyze and detect a substance of interest within the chamber 108 of the device 100. The example reading device 122 includes a light source 124 that emits photons 126 into the chamber 108. In the illustrated example, the photons 126 are scattered by the nanostructures 106 and/or nanoparticles in the sensing material layer 114. In some examples, some of the scattered photons 128 are detected and/or monitored by a spectrometer or photodetector 130 of the reading device 122. In some examples, the reading device 122 uses the detected and/or monitored photons 128 along with appropriate guiding and filtering components to generate substance detection results which can be displayed on a monitor 132. Substance detection results can include, for example, information relating to the presence or absence of a substance/analyte to be detected.

Figure 6:
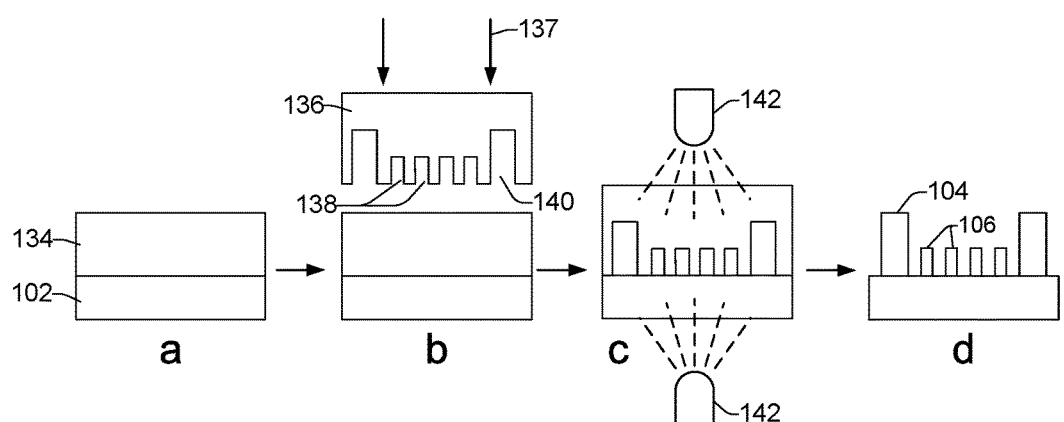
FIG. 6 shows an example process for making a chamber structure and nanostructures on a substrate of a substance detection device.
Figure 7:
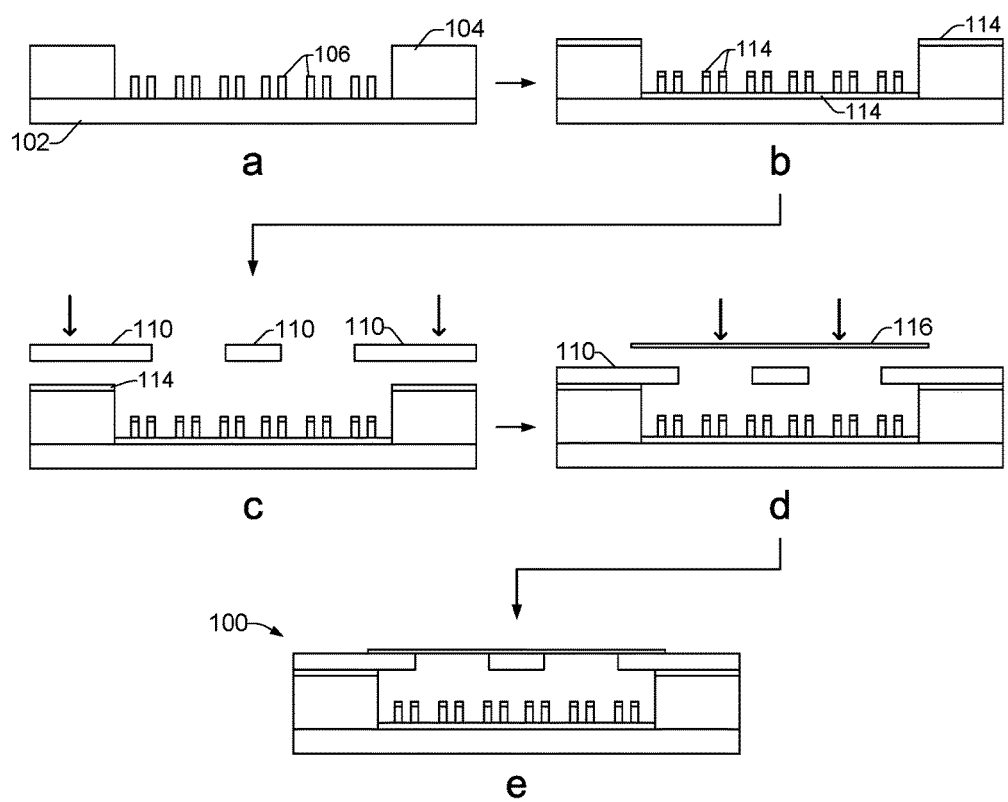
FIG. 7 shows an example process of making a substance detection device by attaching a two-dimensional orifice plate to chamber walls of the device.
Figure 8:
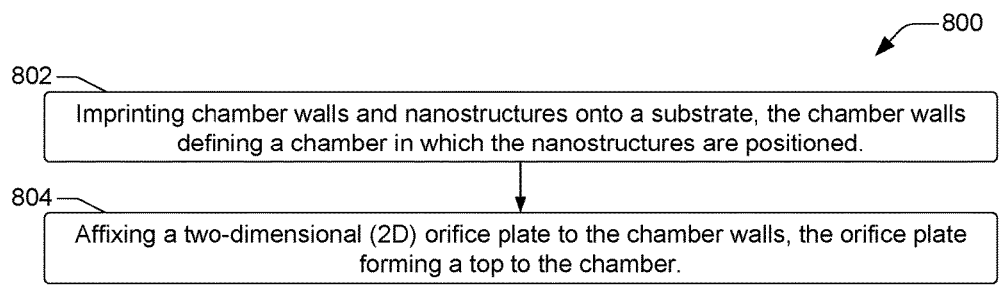
FIG. 8 show a flow diagram of an example method of making a substance detection device that parallels the process illustrated in FIG. 6.
Figure 9:
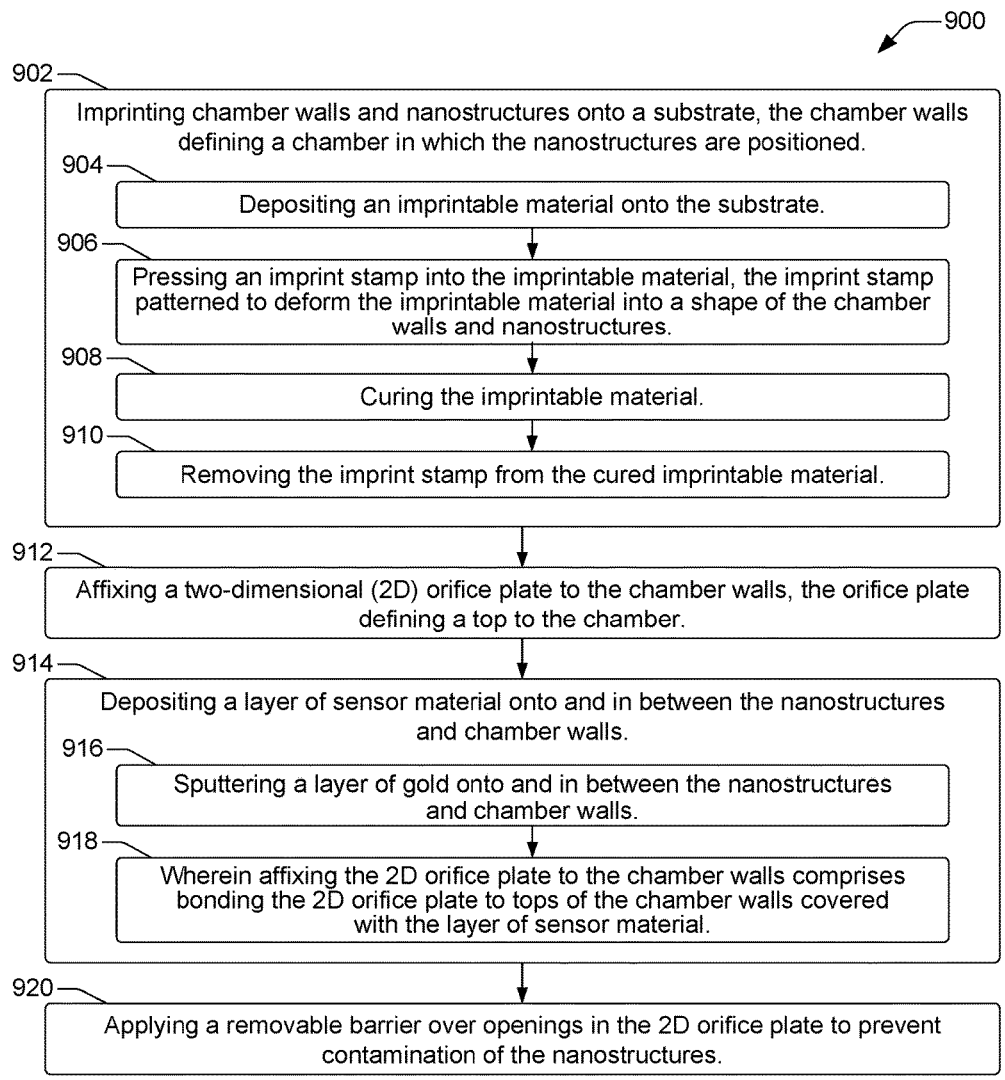
FIG. 9 shows a flow diagram of an alternate example method of making a substance detection device that parallels the processes illustrated in FIGS. 6 and 7.

FIGS. 6 and 7 illustrate an example process for making a substance detection device 100. More specifically, FIG. 6 illustrates an example process for making/fabricating a chamber structure and nanostructures onto a substrate of a substance detection device 100, while FIG. 7 illustrates an example process of completing the fabrication of a substance detection device 100 by attaching a 2D orifice plate to the chamber structure. FIG. 8 is a flow diagram of an example method 800 of making a substance detection device that parallels the processes illustrated in FIGS. 6 and 7. FIG. 9 is a flow diagram of an alternate example method 900 of making a substance detection device that parallels the processes illustrated in FIGS. 6 and 7, including additional details of the process illustrated in FIG. 6.

Referring to FIGS. 6, 8, and 9, an example process for making a chamber structure and nanostructures onto a substrate of a substance detection device 100 is described. FIG. 6 shows a side view of an example substrate 102 that has an imprintable material 134 deposited thereon is shown in FIG. 6. The imprintable material 134 comprises a curable material such as a photo (UV) or thermal curable polymer resist. FIG. 6 (i.e., FIG. 6, a, through 6, d) illustrates the imprinting of chamber walls and nanostructures onto a substrate (FIG. 8, block 802; FIG. 9, block 902). At FIG. 6, a, the imprintable material 134 can be deposited onto the substrate 102 (FIG. 9, block 904) by various methods including spin coating and jetting from a nozzle, such as from an inkjet nozzle. At FIG. 6, b, the imprintable material 134 is imprinted with a master imprint stamp 136. More specifically, the imprint stamp 136 is pressed down into the imprintable material 134 as indicated by arrows 137, to cause a mechanical deformation of the imprint material 134 in the shape of nanometer scale patterns formed on the imprint stamp 136 (FIG. 9, block 906). In the illustrated example, the patterns formed on the imprint stamp include nanostructure patterns 138 and chamber wall patterns 140. Thus, at FIG. 6, b, chamber walls 104 and nanostructures 106 are imprinted onto the substrate 102.

At FIG. 6, c, the imprintable material 134 is cured (FIG. 9, block 908). The cure can be a thermal cure or a UV cure. Thus, heat or UV light 142 can be applied to the imprintable material 134 until it is cured. In some examples, one or the other of the substrate 102 and the imprint stamp 136 can be formed of a transparent material such as fused silica (quartz) in order to enable ultraviolet (UV) curing of the imprintable material 134. Thus, UV light 142 can come through either the substrate 102 or the imprint stamp 136 to cure the imprintable material 134. In some examples, the UV light source 142 can comprise a heat source in the event the imprintable material 134 is thermally curable instead of UV curable.

At FIG. 6, d, the imprint stamp 136 can be removed from the cured imprintable material 134 (FIG. 9, block 910). Removing the imprint stamp 136 leaves behind deformations in the imprintable material 134 formed by the nanometer scale patterns 138 and 140 of the imprint stamp 136. Thus, the cured imprintable material 134 has the shape of the nanostructures 106 and chamber walls 104.

Referring now to FIGS. 7, 8, and 9, an example process of completing the fabrication of a substance detection device 100 by affixing a 2D orifice plate to the chamber walls 104 is described (FIG. 8, block 804; FIG. 9, block 912). As noted above, the orifice plate forms a top to the chamber 108. As shown at FIG. 7, a, chamber walls 104 and nanostructures 106 have been formed on substrate 102 using a nanoimprint process as shown in FIG. 6. At FIG. 7, b, a layer of sensor material 114 is deposited onto and in between the nanostructures 106 and chamber walls 104 (FIG. 9, block 914). Depositing a layer of sensor material can include sputtering a layer of gold or other suitable material onto and in between the nanostructures 106 and chamber walls 104 (FIG. 9, block 916). In addition, as shown at FIG. 7, c, affixing the 2D orifice plate 110 to the chamber walls 104 can comprise bonding the 2D orifice plate to tops of the chamber walls that are covered by the layer of sensor material (FIG. 9, block 918). As shown at FIG. 7, d, a removable barrier or seal 116 can be applied over openings 112 in the 2D orifice plate 110 to prevent contamination of the nanostructures 106 in the chamber 108 (FIG. 9, block 920). The removable seal 116 comprises a hermetic seal that can be made of, for example, polymer tape, plastic material, transparent material, plastic sheeting, foil material (e.g., aluminum, copper, tin, gold), foil sheeting, a membrane, wax and/or Polydimethylsiloxane, and so on. As shown at FIG. 7, e, the fabrication of an example substance detection device 100 is completed upon affixing the 2D orifice plate and removable seal 116.

What is claimed is:

1. A substance detection device comprising:
a substrate comprising nanoimprinted chamber walls and nanostructures, the chamber walls defining a chamber and the nanostructures positioned within the chamber to react to a substance introduced into the chamber; and,
a two-dimensional (2D) orifice plate affixed to the chamber walls and forming a top side of the chamber.

2. A device as in claim 1, further comprising a seal removably affixed to the orifice plate to cover openings in the orifice plate and prevent premature exposure of the nanostructures within the chamber.

3. A device as in claim 1, wherein the chamber walls and nanostructures comprise a cured, imprintable material.

4. A device as in claim 3, wherein the cured, imprintable material comprises a polymer resist.

5. A device as in claim 1, wherein:
the 2D orifice plate comprises a 2D rigid metal orifice plate;
the substrate comprises a flexible substrate; and
the device comprises a partly rigid and partly flexible device.

6. A device as in claim 1, further comprising a layer of sensing material deposited over the substrate to cover tops of the nanostructures, tops of the chamber walls, and areas in between the nanostructures and chamber walls.

7. A device as in claim 6, wherein the 2D orifice plate is bonded to the tops of the chamber walls via the layer of sensing material.

8. A method of making a substance detection device comprising:
imprinting chamber walls and nanostructures onto a substrate, the chamber walls defining a chamber in which the nanostructures are positioned; and
affixing a two-dimensional (2D) orifice plate to the chamber walls, the orifice plate forming a top to the chamber.

9. A method as in claim 8, wherein imprinting comprises:
depositing an imprintable material onto the substrate;
pressing an imprint stamp into the imprintable material, the imprint stamp patterned to deform the imprintable material into a shape of the chamber walls and nanostructures;
curing the imprintable material; and,
removing the imprint stamp from the cured imprintable material.

10. A method as in claim 8, further comprising depositing a layer of sensor material onto and in between the nanostructures and chamber walls.

11. A method as in claim 10, wherein depositing a layer of sensor material comprises sputtering a layer of gold.

12. A method as in claim 10, wherein affixing the 2D orifice plate to the chamber walls comprises bonding the 2D orifice plate to tops of the chamber walls covered with the layer of sensor material.

13. A method as in claim 8, further comprising applying a removable barrier over openings in the 2D orifice plate to prevent contamination of the nanostructures.

14. A partly rigid and partly flexible substance detection device comprising:
a flexible substrate having chamber walls and nanostructures nanoimprinted thereon, the chamber walls defining a chamber in which the nanostructures are positioned; and
a rigid metal two-dimensional (2D) orifice plate bonded to the chamber walls and forming a top side of the chamber.

15. A device as in claim 14, further comprising a sensor material layer that covers tops of the chamber walls to facilitate bonding between the chamber walls and the rigid metal 2D orifice plate and tops of the nanostructures to facilitate sensing of a substance.

* * * * *